(12) United States Patent
Arnold et al.

(10) Patent No.: US 8,642,111 B2
(45) Date of Patent: Feb. 4, 2014

(54) FUNCTIONALIZING A SENSING RIBBON ON A WHISPERING GALLERY MODE MICRORESONATOR USING LIGHT FORCE TO FABRICATE A WHISPERING GALLERY MODE SENSOR

(75) Inventors: Stephen Arnold, New York, NY (US); Stephen Holler, Staten Island, NY (US); Ta Kang Keng, Rego Park, NY (US); Siyka Shopova, Staten Island, NY (US)

(73) Assignee: Polytechnic Institute of New York University, Brooklyn, NY (US)

( * ) Notice: Subject to any disclaimer, the term of this patent is extended or adjusted under 35 U.S.C. 154(b) by 845 days.

(21) Appl. No.: 12/783,367

(22) Filed: May 19, 2010

(65) Prior Publication Data

US 2010/0297363 A1    Nov. 25, 2010

Related U.S. Application Data

(60) Provisional application No. 61/179,567, filed on May 19, 2009.

(51) Int. Cl.
*B05D 3/00* (2006.01)
(52) U.S. Cl.
USPC ......... 427/2.11; 427/2.12; 427/2.13; 427/162
(58) Field of Classification Search
USPC ...................................... 427/2.11, 2.12, 2.13
See application file for complete search history.

(56) References Cited

U.S. PATENT DOCUMENTS

| | | | |
|---|---|---|---|
| 3,984,524 | A | 10/1976 | Alexandrov et al. |
| 4,169,804 | A | 10/1979 | Yapel, Jr. |
| 4,912,087 | A | 3/1990 | Aslam et al. |
| 5,231,533 | A | 7/1993 | Gonokami et al. |
| 5,496,997 | A | 3/1996 | Pope |
| 5,602,102 | A | 2/1997 | Thiele et al. |
| 5,786,219 | A | 7/1998 | Zhang et al. |
| 6,266,459 | B1 | 7/2001 | Walt et al. |
| 6,389,197 | B1 | 5/2002 | Iltchenko et al. |
| 6,473,218 | B1 | 10/2002 | Maleki et al. |
| 6,490,039 | B2 | 12/2002 | Maleki et al. |
| 6,507,684 | B2 | 1/2003 | Tapalian et al. |
| 6,583,399 | B1 | 6/2003 | Hunziker et al. |
| 2001/0033587 | A1 | 10/2001 | Painter et al. |
| 2002/0080842 | A1 | 6/2002 | An et al. |
| 2002/0097401 | A1 | 7/2002 | Maleki et al. |
| 2004/0023396 | A1 | 2/2004 | Boyd et al. |

OTHER PUBLICATIONS

A. Serpengüzel, S. Arnold and G. Griffel, "Excitation of Resonances of Microspheres on an Optical Fiber," *Optics Letters*, vol. 20, No. 7, pp. 654-656, (Apr. 1995).

Ganapolshii, et al., "A Sapphire Sphere Resonator for the Measurement of Low Dielectric Losses in the Millimetre-Wave Range in Liquids," *Measurement Science and Technology*, vol. 7, pp. 1016-1022 (1997).

(Continued)

*Primary Examiner* — Dah-Wei Yuan
*Assistant Examiner* — Andrew Bowman
(74) *Attorney, Agent, or Firm* — John C. Pokotylo; Straub & Pokotylo

(57) ABSTRACT

Methods using light force to fabricate WGM sensors including microresonators having target receptors selectively and substantially provided at only ribbon area of the microresonators.

20 Claims, 4 Drawing Sheets

(56) References Cited

OTHER PUBLICATIONS

Hill, et al., "Fluorescence Image of a Single Molecule in a Microsphere: Model," *Journal of the Optical Society of America B*, vol. 16, No. 11, pp. 1868-1873 (1999).

Cai, Ming; Hunziker, Guido; Vahala, Kerry; "Fiber-Optic Ad-Drop Device Based on a Silica Microsphere-Whispering Gallery Mode System," *IEEE Photonics Technology Letters*, vol. 11, No. 6 (Jun. 1999).

Rosenberger, et al., "Evanescent-Wave Sensor Using Microsphere Whispering-Gallery Modes," *Proceedings of SPIE*, vol. 3930, pp. 186-192 (2000).

Blair, et al., "Resonant-Enhanced Evanescent-Wave Fluorescence Biosensing with Cylindrical Optical Cavities," *Applied Optics*, vol. 40, No. 4, pp. 570-582 (Feb. 2001).

S. Arnold, "Microspheres, Photonic Atoms and the Physics of Nothing," *American Scientist*, vol. 89, pp. 414-421 (Sep.-Oct. 2001).

Boyd, et al., "Sensitive Disk Resonator Photonic Biosensor," *Applied Optics*, vol. 40, No. 31, pp. 5742-5747 (Nov. 2001).

Airola, et al., "Resonant Cavity Optical Biosensors for the Detection of Nucleic Acid Hybridization," Proceedings of SPIE, vol. 4625, pp. 29-37 (2002).

Vollmer, Frank; Arnold, Stephen; Braun, Dieter; Teraoka, Iwao; "Multiplexed DNA Quantification by Spectroscopic Shift of Two Microsphere Cavities," *Biophysical Journal*, vol. 85, pp. 1974-1979 (Sep. 2003).

FUNCTIONALIZING A SENSING RIBBON ON A WHISPERING GALLERY MODE MICRORESONATOR USING LIGHT FORCE TO FABRICATE A WHISPERING GALLERY MODE SENSOR

RELATED APPLICATION(S)

This application claims benefit to U.S. Provisional Application Ser. No. 61/179,567 ("the '567 provisional"), titled "LIGHT FORCE FUNCTIONALIZATION OF WHISPERING GALLERY MODE BIOSENSORS", filed on May 19, 2009, and listing Stephen Arnold, David Keng, Stephen Holler and Siyka Shopova as the inventors. That application is expressly incorporated herein by reference. The scope of the present invention is not limited to any requirements of the specific embodiments in that application.

FEDERAL FUNDING

This invention was made with Government support and the Government may have certain rights in the invention as provided for by grant number 0522668 awarded by the National Science Foundation.

BACKGROUND OF THE INVENTION

1. Field of the Invention

The present invention concerns the fabrication of whispering gallery mode ("WGM") sensors that can detect the presence of, identify the composition of, and/or measure an amount or concentration of substances (referred to generally as "target entities" or "target analytes"), such as chemical or biological entities, even in amounts as small as a single protein or virus particle. More specifically, the present invention concerns methods and apparatus to selectively functionalize a sensing ribbon on a resonator of a WGM sensor.

2. Background Information

There exists an ongoing need for sensors for detecting various "target entities" such as, for example, infectious agents (e.g., viruses, bacteria, etc.), toxins, small amounts of proteins, DNA, RNA, etc. Similarly, there exists an ongoing need for sensors for measuring DNA hybridization, protein adsorption, biomolecular mass, etc.

One known device used to detect the presence of small particles is a microsphere sensor coupled to an optical waveguide (e.g., an eroded optical fiber), one end of which is optically coupled with a light source and the other end with a light detector. Whispering gallery modes of the light circulating within the microsphere can be observed in optical signals detected at the detector. Target entities selectively captured (e.g., adsorbed) by target receptors on the surface of the microsphere may shift the whispering gallery modes. These so-called WGM sensors have emerged as an important optical tool for detection and analysis of trace quantities of biological materials. These WGM sensors have been employed in a host of applications including the detection of virus and bacteria, measurement of DNA hybridization and protein adsorption, and biomolecular mass determination.

Examples of such WGM sensors are described in U.S. Pat. No. 7,491,491 (referred to as "the '491 patent" and incorporated herein by reference). Although the '491 patent mainly describes microsphere-based WGM sensors, such sensors may employ microresonators (referred to generally as "resonators") with geometries other than microspheres, such as, for example, (micro-)cylinders, (micro-)rings, (micro-)disks, (micro-)toroids, (micro-)racetracks, (micro-)bottle resonators, and any other geometry capable of supporting WGM. Each of these configurations relies on the inherent sensitivity of the whispering gallery mode resonances within the resonator to changes in the external environment to provide a sensitive detection mechanism.

However, known WGM sensors may have limits on the minimum size of the particles that may be detected and/or identified, or may have challenges associated with their fabrication More specifically, in many WGM sensors, bulk chemical techniques are used to sensitize the resonator surface to the target entity. This can result in variations in the surface sensitivity to binding events, and thus lead to a corresponding variability of the measured signal during the transduction event. To eliminate such variations (which can impact, for example, a size determination of the target entity), it is preferred that the target entities be captured at an optimal sensing region. For example, in spherical micro-resonators, the optimal sensing region of the surface corresponds to the equatorial perimeter about which the whispering gallery mode is stimulated. However, such localization of target receptors on the resonator surface is not possible with traditional bulk chemistry approaches.

U.S. Patent Application Publication No. 2004-0137478 (referred to as "the '478 publication" and incorporated herein by reference), titled "ENHANCING THE SENSITIVITY OF A MICROSPHERE SENSOR," discusses increasing the sensitivity of WGM sensors to the point where an individual protein molecule, virus particle, or other small target entity can be detected and identified. More specifically, the '478 publication espouses using a microsphere specially treated or silanized in the equator region to create a band (e.g., a narrow band) of target receptors such that the target receptors are substantially limited to a highly sensitive region near the equator of the microsphere. The '478 publication discusses fabricating microsphere sensors having target receptors substantially only at a sensitive equator region of a microsphere's surface by (i) selecting a microsphere with properties (refractive index ("RI") and radius) suited to the intended sensing application, (ii) optically coupling an eroded optical fiber with the microsphere at an equator, (iii) coating the microsphere with a UV reactive binding agent, such as an epoxy, (iv) selectively establishing an equator region with receptor material by immersing the microsphere in a solution with target receptors, (e.g., of selected amines) and irradiating the equator band with UV light coupled into the microsphere through the eroded optical fiber causing a reaction between the target receptors in the solution and the binding agent, (v) washing the resulting sphere, and (vi) establishing the non-equator region as a non-interacting region (e.g., by immersing the microsphere in a solution of mono-secondary amines, irradiating the entire surface with UV light (e.g., from an external lamp) causing a reaction between the mono-secondary amines and any un-reacted binding agent, and washing).

Unfortunately, however, the fabrication technique discussed in the '478 publication has not worked well in practice. For example, in the approach described in the '478 publication, a UV light source must be made to propagate through the optical waveguide to couple evanescently with the microresonator in order to prepare the device for surface modification. The waveguide employed might be the same in which the sensing laser would propagate However, this is impractical because most optical waveguides are extremely lossy in the ultraviolet spectral region and the sensitizing laser used in fabrication would suffer significant absorption prior to reaching the microresonator. Furthermore, an optical waveguide that is single mode for the sensing laser would inherently be multimode for the UV laser. Such multimode operation is undesirable. In addition, the UV light source would stimulate different modes than those that would be used during the sensing mode of operation. Finally, the UV laser will not produce a strong "light force" pulling the target receptors to the preferred region during fabrication.

In light of the above discussion, it is clear that there is a need to provide improved WGM sensors, as well as improved techniques for fabricating such WGM sensors.

SUMMARY OF THE INVENTION

Embodiments consistent with the present invention may be used to fabricate WGM sensors having improved sensitivity and/or a more uniform response to target entities by (a) immersing a microresonator in a solution including target receptors; (b) inducing light to resonate within the microresonator, thereby generating an attractive force between a ribbon surface area of the microresonator and the target receptors in the solution, the attractive force being sufficiently strong to pull the target receptors close enough to the ribbon surface area of the microresonator to permit chemical bonds to hold the target receptors to the ribbon surface area of the microresonator, wherein non-ribbon surface areas of the microresonator are substantially free of target receptors; and (c) passivating the non-ribbon surface areas of the microresonator.

DETAILED DESCRIPTION

The present invention may involve improved methods and apparatus for fabricating various WGM sensors. The following description is presented to enable one skilled in the art to make and use the invention, and is provided in the context of particular applications and their requirements. Thus, the following description of embodiments consistent with the present invention provides illustration and description, but is not intended to be exhaustive or to limit the present invention to the precise form disclosed. Various modifications to the disclosed embodiments will be apparent to those skilled in the art, and the general principles set forth below may be applied to other embodiments and applications. For example, although a series of acts may be described with reference to a flow diagram, the order of acts may differ in other implementations when the performance of one act is not dependent on the completion of another act. Further, non-dependent acts may be performed in parallel. Also, as used herein, the article "a" is intended to include one or more items. Where only one item is intended, the term "one" or similar language is used. In the following, "information" may refer to the actual information, or a pointer to, identifier of, or location of such information. No element, act or instruction used in the description should be construed as critical or essential to the present invention unless explicitly described as such. Thus, the present invention is not intended to be limited to the embodiments shown and the inventors regard their invention to include any patentable subject matter described.

Figure 1:
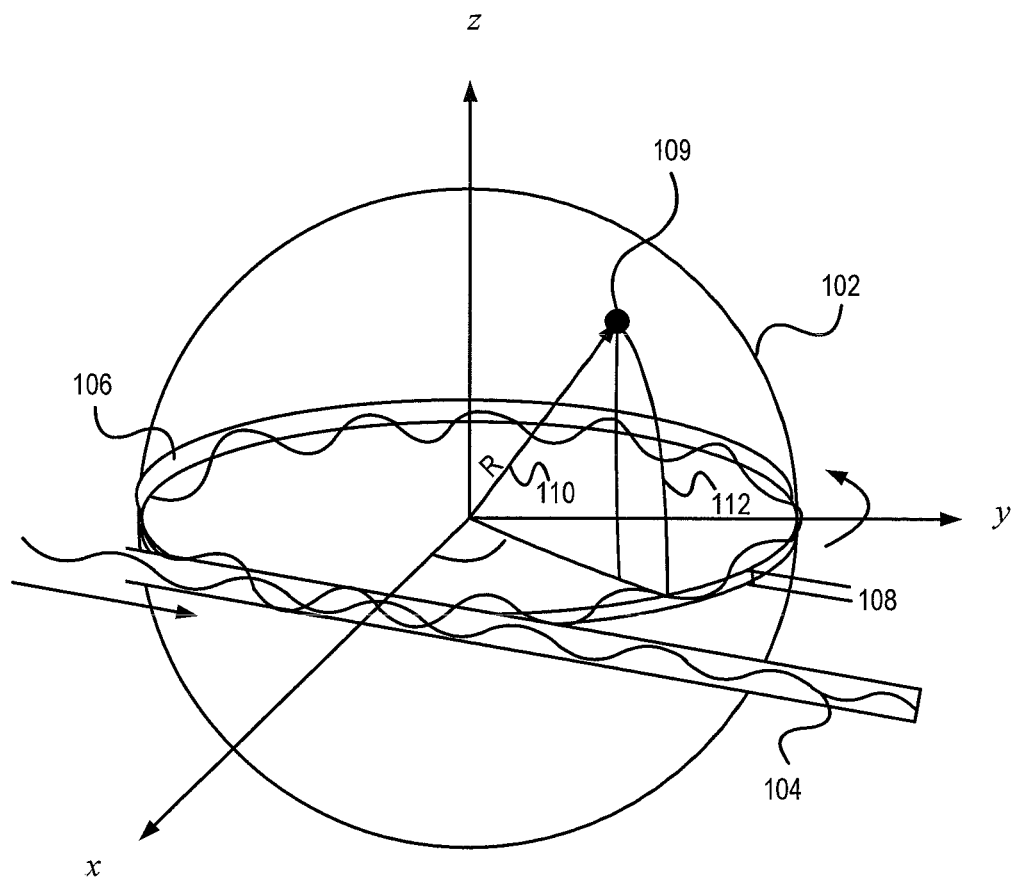
FIG. 1 illustrates an exemplary microsphere WGM sensor that may be fabricated in a manner consistent with the present invention.

Exemplary Enhanced Microsphere Sensor which May be Fabricated by Exemplary Techniques Consistent with the Present Invention FIG. 1 is an illustration of a microsphere sensor 100 which may be fabricated in a manner consistent with the present invention. The microsphere resonator 102 is optically coupled with an eroded optical fiber 104 at a point or segment on the equator 106 of the microsphere 102. In accordance with the invention, a (narrow) band (also referred to as a "ribbon") of target receptors 108 has been selectively formed on the equator 106 of the microsphere 102. This limited "ribbon" of target receptors is in contrast to many known microsphere sensors which may have target receptors on the entire surface of the microsphere, or over large regions of the surface. In such known microsphere sensors, sensitivity to each captured target entity may vary depending on the location r, 109 on the microsphere surface that the target entity is captured by the target receptors. In such cases, the microsphere sensor may require that a large number of target entities be captured by the target receptors to detect, quantify, and/or identify the target (or unknown) entity. By restricting target receptors to the high sensitivity "ribbon" area 108, where the level of change caused by a single target entity is identifiable and relatively uniform in magnitude, WGM sensors fabricated in a manner consistent with the present invention can be used to make each target entity captured by a target receptor significant and even facilitate detection and/or identification based on a single target entity particle.

A frequency shift in a resonance mode, due to the capture of a target (or unknown) entity by a target receptor, in the high sensitivity receptor "ribbon" 108, may be detected by a detector optically coupled with the microsphere sensor 100. For microsphere sensors 100 provided with the high sensitivity receptor "ribbon" 108, the level of frequency shift, due to the adsorption of a target entity, may vary (approximately) as $1/R^{5/2}$, where R 110 is the radius of the microsphere 102.

In accordance with at least some exemplary embodiments consistent with the present invention, the sensitivity of the microsphere 102 may be further increased by reducing the size of the microsphere 102. That is, microspheres with a radius of approximately 30-300 µm are common. Embodiments consistent with the present invention may use a microsphere with a radius of 300 µm or less, and in some embodiments with a radius of approximately 3.6-10 µm. The microsphere's sensitivity may be further increased by changing the refractive index of the material used in the microsphere 102 to a material with a higher refractive index. That is, silica microspheres having a refractive index of 1.47 are common. Embodiments consistent with the present invention may provide microspheres of an alternative material, e.g., amorphous sapphire, with refractive index 1.7.

The refractive index (RI) selected for the microsphere 102 and the range of radii 110 of the microsphere 102 can be matched to the target entity or group of target entities which the microsphere sensor 100 is intended to detect and/or identify. For a high refractive index material (e.g., amorphous sapphire), the microsphere radius is preferably between 3.6 to 10 µm when it is desired to detect 1 molecule of a target entity of approximately 200,000 Da. For larger target entities, the radius 110 could be increased in inverse proportion to the molecular weight of the target entity. For larger target entities (e.g., target entities or molecules of several million Da), a material with a relatively lower refractive index could be selected for the microsphere 102. For example, using a silica microsphere 102, which is a material used in known microspheres, with an index of refraction=1.47 in water, large target entities may be detected; however, the minimum size of the silica microsphere is limited to a radius 110 of approximately 75 μm. In contrast, using amorphous sapphire microspheres (having a refractive index=1.7 in water), allows the size of the microsphere 102 to be reduced to a radius 110 of approximately 3.6 μm, allowing smaller size target entity molecules to be detected. Microresonators with other radii and other refractive indices may be used in a manner consistent with the present invention. (Note that some microresonator geometries might not have a radius.)

Exemplary Fabrication of an Enhanced Microsphere Sensor

The '567 provisional describes the "carousel trapping" of nanoparticles in a solution in which a resonance is induced in a WGM resonator. Basically, a nanoparticle may be trapped in a radial potential well defined by the combination of two exponential forces—a long-range attractive interaction (believed to be caused by the light resonating within the resonator), and a short-range repulsive interaction (believed to be caused by surface repulsion between ionized silanol groups on the silica resonator and the negatively charged polystyrene nanoparticle). The trapped nanoparticle is driven to orbit the resonator (apparently due to the WGM's tangential momentum flow).

Embodiments consistent with the present invention exploit this phenomenon to functionalize a ribbon on the WGM resonator surface with target receptors. More specifically, target receptors (examples of which are described below) are used rather than the polystyrene nanoparticles. Since many target receptors (e.g., proteins) will have a negative charge, or can be made to have a negative charge, they will similarly be subject to long-range attractive interactions, and short-range repulsive interactions. However, in embodiments consistent with the present invention, the range of the electrostatic repulsion is effectively decreased to such an extent that the target receptors are pulled toward the surface of the resonator, where they are chemically bound to the surface of the resonator. (Note that although the '567 provision describes van der Waals interactions holding a nanoparticle, in embodiments consistent with the present invention, the target receptors will typically be held to the surface of the resonator by stronger chemical bonds, such as covalent bonds for example, which will hold the target receptors on the resonator surface even after the light resonance is removed or the surface is "washed".) As one example, amine groups on the surface of the resonator may become covalently bound with antibodies provided with a carboxyl functional group.

At least some embodiments consistent with the present invention may decrease the short-range repulsive interaction by increasing the ionic conductivity of the solution (e.g., an aqueous (perhaps buffered) solution such as water, phosphate buffered saline, "heavy water" ($D_2O$), etc.) including the target receptors, in which the resonator is immersed. In some embodiments consistent with the present invention, the ionic conductivity of the solution is increased by adding NaCl to the solution.

As should be appreciated from the foregoing, a long-range attractive interaction between the light resonating within the resonator and the target receptors (this attractive interaction is referred to simply as "light force"), can be used to selectively functionalize only the desired ribbon region of the resonator with target receptors.

Figure 2:
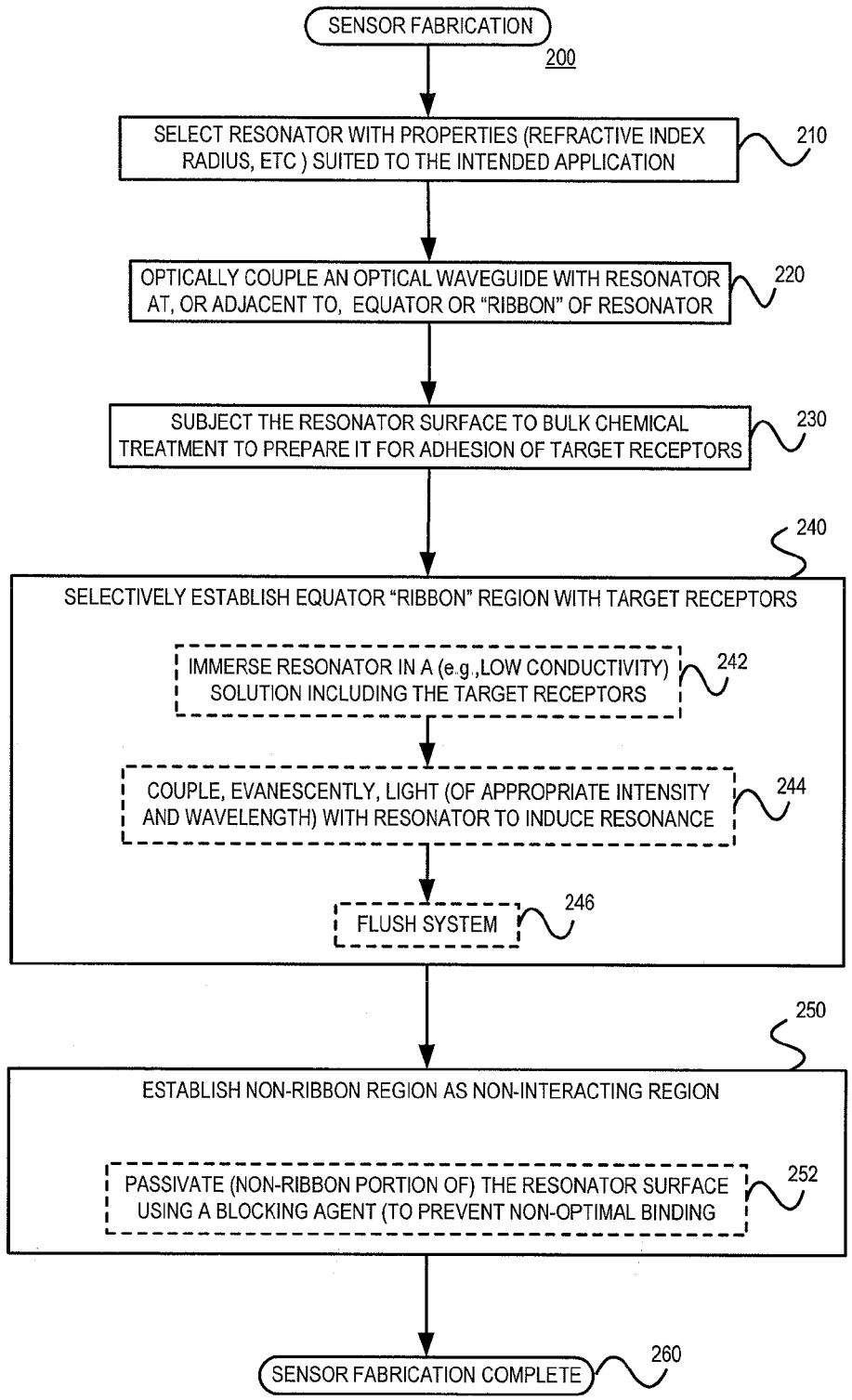
FIG. 2 is a flowchart illustrating an exemplary method for fabricating a WGM sensor in a manner consistent with the present invention.

With the foregoing in mind, an exemplary method 200 for selectively functionalizing a preferred ribbon region of the surface of a resonator with target receptors, using light force, is described with reference to FIG. 2. The remainder of the surface of the resonator may be made chemically inert so that target entities that interact with the resonator will only adhere to (target receptors on) the surface of the resonator on the preferred ribbon region.

A resonator with properties (e.g., refractive index, radius, etc.) suitable for the intended detection and/or measuring application is selected. (Block 210) The selected resonator is optically (and perhaps mechanically) coupled with an optical waveguide. (Block 220) The resonator surface may be subjected to a bulk chemical treatment to prepare it for adhesion (e.g., via chemical bonding, such as covalent bonding) of the target receptors (to which the complementary target entities will selectively bind). (Block 230) Then, the "ribbon" region of the surface of the resonator is selectively established with target receptors. (Block 240) This may be done by immersing the resonator in a low conductivity solution including the target receptors (Block 242), coupling, evanescently, light (of appropriate intensity and wavelength) from the optical waveguide into the resonator to induce resonance within the resonator (Block 244), and finally flushing the system (Block 246). The resonator surface is then passivated using a blocking agent to prevent non-optimal binding (e.g., non-specific binging of non-target entities in regions that would have a minimal, though measurable effect during sensing, as well as non-optimal binding of target entities in such regions, which would result in a non-ideal response) to the surface of the resonator (Block 250), after which the sensor fabrication is complete (Node 260).

Referring back to block 230, in an exemplary WGM sensor in which it is desired to attach antibodies, one might aminosilanize the resonator surface using APTES silane coupling agent. Doing so will form a surface with covalently bound silane surface with amine groups exposed for bonding to the target antibodies. This will work on silica surfaces, as well as silicon nitride, silicon, or other materials on which an oxide layer forms or may be deposited after fabrication.

Referring back to block 244, a pump laser sourcing light into the optical waveguide may be adjusted so that it stimulates a resonance within the resonator, which will cause a build-up of optical power within the resonator. The evanescent field associated with the WGM will extend into the solution and provide an intensity gradient attractive force that will draw the target receptors to the surface of the resonator at the preferred ribbon region. In the case of antibody attachment to an aminosilanized surface, once at the surface, a carboxyl group on the antibodies will bind with the amine group to securely fasten them to the surface at the preferred ribbon location, where they will be well-positioned for later sensing.

Referring back to block 252, the passivation does not affect the previously bound ribbon of target receptors (which remain active for sensing of the target entity). For example, in the case of antibodies, after the system is flushed to remove residual antibodies, it may be subsequently exposed to an amine blocking agent such as Sulfo-NHS acetate. This will passivate the resonator surface, thereby preventing any non-specific binding to the aminosilanized resonator when used as a sensor. However, the antibody (target receptor) coated ribbon region of the resonator surface is unaffected and remains available for sensing target entities during sensing.

Naturally, other fabrication methods with other acts can be used. Further, other materials (e.g., for the resonator, for the bulk chemical treatment, for the solution, and/or for the target receptors, etc.), and/or different parameters (e.g., resonator diameter, solution conductivity, laser wavelength, and/or laser intensity, etc.) may be used (e.g., depending on the target entity to be sensed).

Exemplary System in which the Fabricated Enhanced WGM Sensor May be Used

Figure 3:
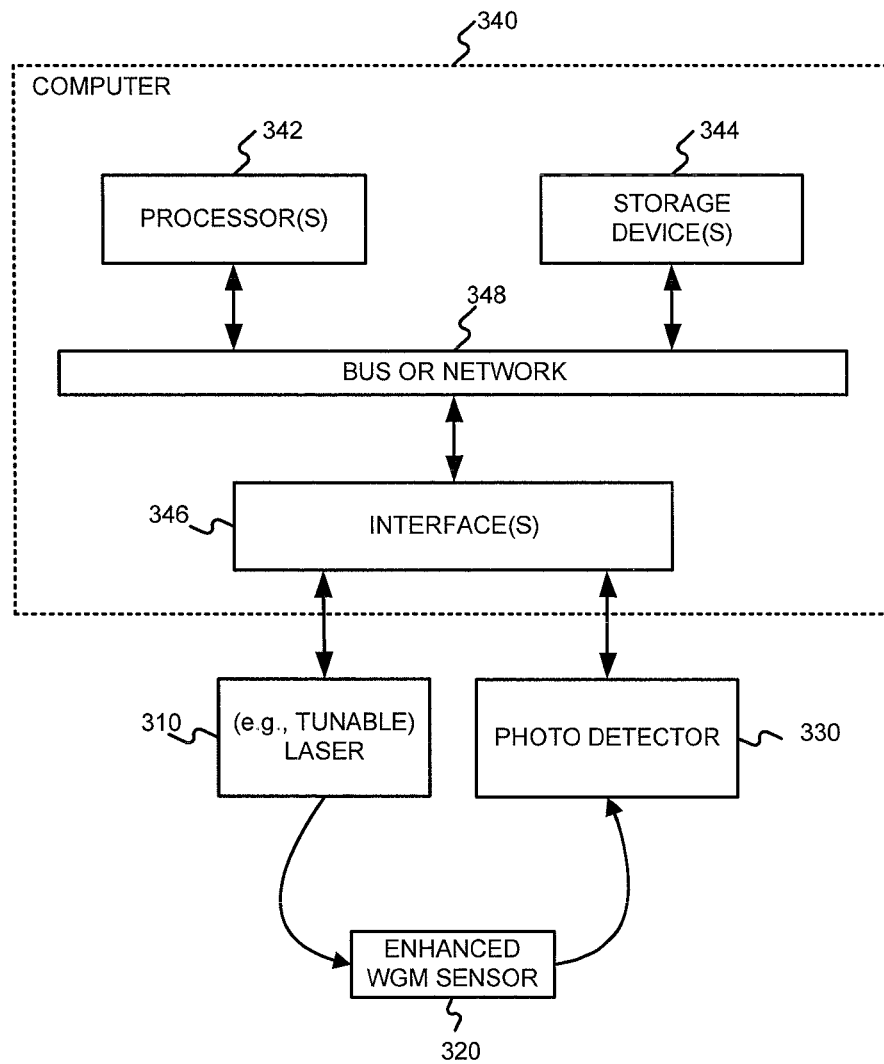
FIG. 3 is a block diagram of an exemplary detection system which may use a WGM sensor fabricated in a manner consistent with the present invention.

FIG. 3 is a block diagram of exemplary sensor detection system 300 which may use the fabricated enhanced WGM sensor for detecting and/or identifying target entities such as biomolecules (e.g. proteins, virus particles, etc.). The sensitivity of the WGM sensor 320 has been enhanced over known systems such that single protein or other small entity detection and identification are possible. Naturally, less sensitive WGM sensors fabricated in a manner consistent with the present invention may be used.

Sensor detection system 300 may include a laser 310, a WGM sensor 320, an optical detector, such as a photo detector 330, and a computer system 340. The computer system 340 includes at least one processor 342, at least one storage device 344 (e.g., RAM, ROM, flash memory, computer readable storage medium, etc.), at least one interface 346, and at least one bus or network 348 over which the various elements may interchange data and information.

The tunable laser 310 may be controlled to emit light (of an appropriate wavelength and intensity) into or through the WGM sensor 320. Photo detector 330 may detect light from the WGM sensor 320. The evaluation of changes in signal output from photo detector 320 may be used to determine the existence of, or the amount of, a target entity that is received by the target receptors of the WGM sensor 320. In systems 300 including a computer 340, the processor(s) 342 under the direction of routines in memory 344, may control the laser 310 through an interface(s) 346. The processor(s) 342 may receive output signaling from photo detector 330 through an interface(s) 346 and process the signaling to determine the existence, and/or amount, of the target entity sensed.

The WGM sensor 320 may have any of a number of possible configurations including a single microresonator sensing head, a multiple microresonator sensing head using different receptors on different microresonators, and a multiple microresonator sensing head including at least one microresonator without receptors to be used to characterize and remove common mode noise. (See, e.g., the '491 patent.)

In some embodiments, the sensor detection system 300 may be implemented using one or more modules. Such modules may be implemented using software, hardware, or a combination of software and hardware.

Figure 4:
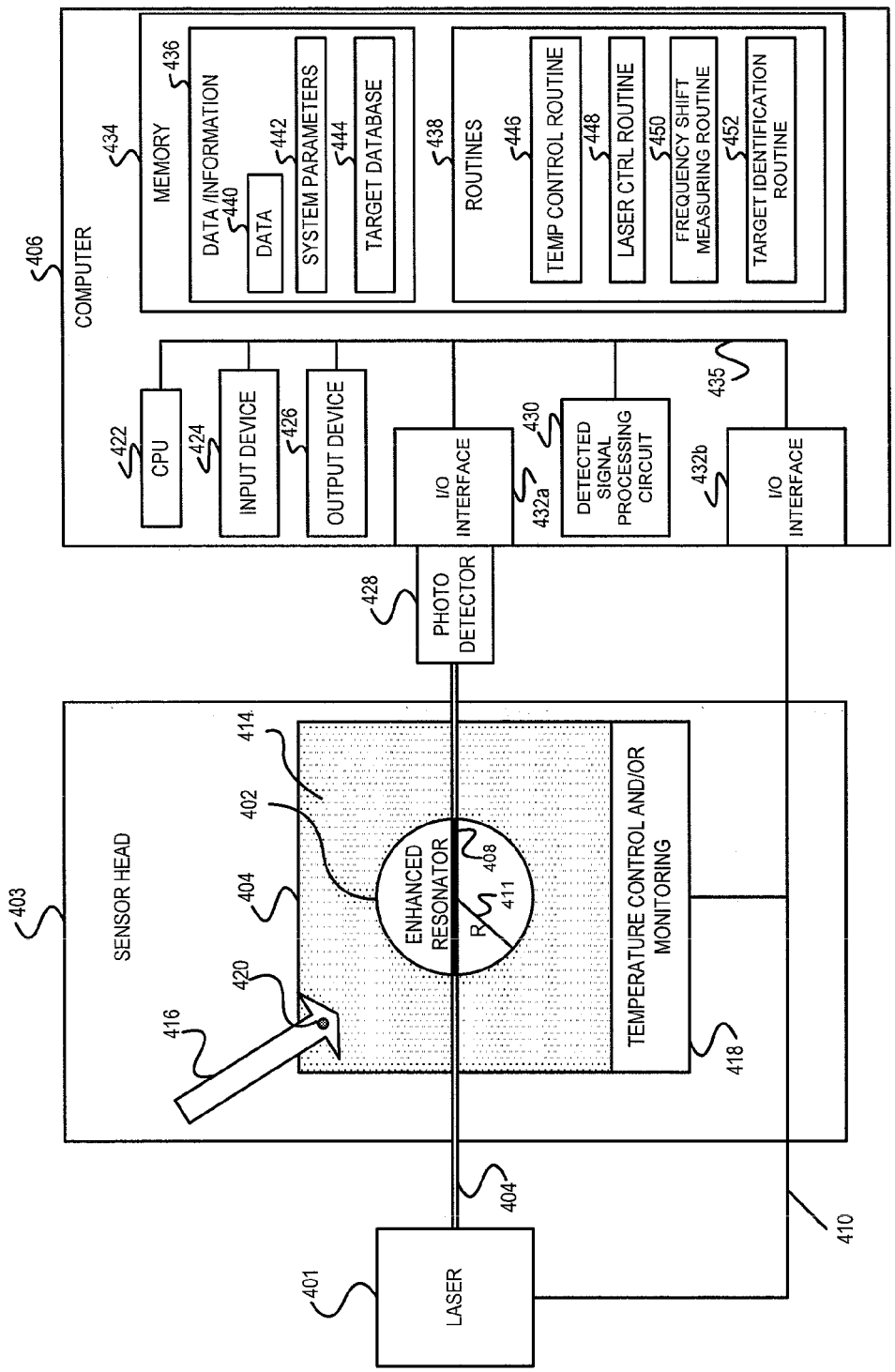
FIG. 4 is an exemplary detection system which may use a WGM sensor fabricated in a manner consistent with the present invention.

FIG. 4 illustrates an exemplary detection system 400 which may be one possible exemplary embodiment of system 300. Detection system 400 may include a tunable narrow linewidth (<5 MHz) laser (such as, for example, a distributed feedback ("DFB") laser, a distributed Bragg reflector ("DBR") laser, an external cavity laser ("ECL"), a fiber laser, laser light due to harmonic generation or optical parametric generation ("OPG") including, but not limited to, second harmonic generation ("SHG"), sum frequency generation ("SFG"), difference frequency generation ("DFG"), etc.) 401, a WGM head 402 including a microsphere containment vessel 404, and an optical detector, e.g., a photo detector 428 which may be coupled to a computer 406 through I/O interface 432. The laser 401 may be, e.g., a blue diode laser with external cavity operating at a wavelength of about 400 nm, generally available lasers having a wavelength of about 1.3 or 1.5 μm, external cavity (e.g., diode) lasers with a wavelength of 1060 nm, etc. Generally, a shorter wavelength (e.g., visible light) is better because absorption of the resonant light by the surrounding medium may degrade the quality of the resonance and reduce the system sensitivity. However, there is a trade-off in the extent to which the short wavelength field permeates the surrounding medium. This reduced reach of the short wavelength source may limit the extent to which the light force may draw target receptors towards to the surface of the microresonator. The laser 401 selected for system 400 may operate at a wavelength including, but not limited to, the foregoing wavelengths. Other wavelengths may be used, perhaps in concert with other sensor design changes, to reduce the size of the smallest detectable protein polarizability.

The microresonator containment vessel 404 may include a microresonator 402 including a ribbon 408 of target receptors, an aqueous medium 414, a target entity injection element 416, and a temperature control and/or monitoring device 418. Microresonator 402 may include one or more of the features described above. Target entity injection element 416, may hold and control the release of a sample including a target entity 420, e.g., a protein molecule. The target entity 420 may diffuse through the aqueous medium (e.g., water) 414 to the microresonator's surface where it may be adsorbed in the ribbon of target receptors 408, and shifts the frequency of the resonant modes. Temperature control and/or monitoring device 418 may include temperature sensors, heaters, and regulation circuitry, for reporting the temperature of the vessel 404, microresonator 402, and/or aqueous medium 414 to the computer system 406, and/or regulating the temperatures.

In some embodiments, multiple microresonators 402 may be used in the same aqueous medium 414. In some embodiments, multiple microresonator WGM sensors, each sensor customized (with specific complementary receptors, specific physical characteristics, and a specific sized ribbon of target receptors) for detection of a specific target entity, may be coupled with the detection system. In some embodiments, microresonators similar or identical to sensor microresonators, except without a target receptor material, may be included. Those microresonators without target receptor material may provide information on resonance characteristics changes, due to environmental disturbances and may be used to characterize "common mode noise".

In some embodiments, the microresonator 402 may be inserted and removed from the microresonator containment vessel 404. In some embodiments, adsorption of target entities onto the microresonator surface at the ribbon 408 of target receptors may occur while the microresonator 402 is removed from the aqueous medium 414, and the microresonator 402 may be inserted into the medium 414 for measurement purposes.

In some embodiments, the microresonator 402 sensor might not be situated in an aqueous medium 414, but rather in a gaseous medium (e.g., air). In some embodiments, microresonator 402 sensor may not be situated in a containment vessel 404, but rather may be placed in an open environment. In some embodiments, an injection element 416 might not be used. In some embodiments, gaseous or aqueous medium, which may contain target entities, may be directed or forced to pass over the microresonator WGM sensor.

The photo detector 428 may provide data to a computer system 406 through I/O interface 432. In some embodiments the photo detector 428 may be included as part of the computer system 406. The computer system 406 may include a processor (e.g., a CPU) 422, an input device 424, an output device 426, a detected signal processing circuit 430, I/O interfaces 432a,b, and memory 434 coupled together via bus or network 435 over which the various elements may interchange data and information. Memory 434 may include data/information 436 and routines 438. Data/information 436 may include data 440, system parameters 442, and target entity information 444. Routines 438 may include a temperature control routine 446, a laser control routine 448, a frequency shift measurement routine 450, and/or a target identification routine 452. The processor 422 may be used to execute the routines 438 and use the data/information 436 in memory 434 to detect and identify substances such as biomolecules (e.g., proteins or virus particles, etc.), such as described with respect to FIG. 9 of the '479 publication. The input device 424 may include keyboards, keypads, etc., and may be used to notify the computer system 406, that a target entity 420 has been released into aqueous medium 414. Output devices 426 may include displays, printers, speakers, etc. which may indicate temperature stabilization, prompts to release target entities 420, detected frequency shifts, and identified target entities 420

The system 400 may operate as follows. Photo detector 428 receives the light transmission from the laser 401, which has been altered by the resonant modes of WGMs of microresonator 402 and shifts in resonant mode due to adsorbed target entities 420, and converts the optical signal to an electrical signal. Detected signal processing circuit 430 receives the electrical signal from the photo detector 428 and detects such resonance modes (manifested as dips in the transmitted signal which correspond to resonant modes). I/O interface 432 may include line drivers and receivers, A/D converters, D/A converters, frequency counters, etc. Data 440 may include data collected on the transmitted signal, e.g., frequency, detected resonant modes, shifts detected in resonant modes, and temperature data of the microresonator 402 and/or aqueous medium 414

System parameters 442 may include frequency and intensity of the laser 401, radius 411 of the microresonator 402, parameters defining a specially treated target reception region 408 on the microresonator 402, stabilization temperature, index of refraction of the microresonator 402, index of refraction of the aqueous medium 414, thermal models, and calibration parameters associated with the system 400. Target entity information (e.g., in the form of a database) 444 may include look-up tables associating step changes or level shifts in the frequency of the modes observed with specific target entities 420 (e.g., protein molecules such as thyroglobulin, ferritin, or virus particles such as lambda phage). Temperature control routine 446 may forward temperature sensor information from temperature control and/or monitoring device 418, and may control circuitry within device 418 to maintain temperature stabilization of the microresonator 402 and/or aqueous medium 414 at pre-determined levels. Laser control routine 448 may control and monitor the tunable DFB laser 401 to maintain a detectable WGM signal at the photo detector 428 and provide current precise laser frequency information to the computer system 406. Frequency shift measuring routine 450 processes information from the detected signal processing circuit 430 to detect step changes of shifts in mode frequencies with time. Target identification routine 452 uses the output of the frequency shift measuring routine 450 to match the step level changes to a corresponding target entity, e.g., a specific protein molecule or virus particle such as a lambda phage virus particle.

The tunable laser 401 is optically coupled with the microresonator 402, and the photodetector 428 via an optical waveguide 404 (e.g., an optical fiber eroded at the attachment point to the microresonator 402). This allows light being transmitted from the laser 401 to the photodetector 428 to be coupled into a WGM of the microresonator 402, create detectable resonant modes in the transmission, and create detectable frequency shifts in the resonant modes in response to adsorbed target entities on the microresonator 402. In other embodiments, the light from the laser 401 is coupled into the microresonator 402 via means other than a physically continuous optical waveguide such as, for example, via lenses, splitters, etc. Electrically, the laser 401 may be coupled to the temperature control/monitoring circuitry 418 of the microresonator containment vessel 404 and the I/O interface 432 of the computer system 406 via bus 410 over which measurement signals and control information is exchanged.

As should be appreciated from the foregoing, WGM sensors fabricated in a manner consistent with the present invention may be used in systems and with methods such as those described in the '478 publication. Naturally, an enhanced WGM sensor fabricated in a manner consistent with the present invention may be used in other detection and/or sensing systems.

Refinements, Alternatives, and Extensions

Although exemplary embodiments consistent with the present invention describe fabricating microsphere sensors, the light force functionalization fabrication technique may be used to functionalize other configurations of WGM sensors such as, for example, (micro-)cylinders, (micro-)disks, (micro-)rings, (micro-)racetrack, (micro-)bottle resonator and (micro-)toroids (or any other resonator geometry that can support a WGM).

Although the resonator was described as being silica or amorphous sapphire, other materials for a resonator such as glass, silicon, silicon nitride, silicon oxynitride, gallium nitride (GaN), gallium arsenide (GaAs), indium arsenide (InAs), etc., may be used in a manner consistent with the present invention. Various chemical processes, known to those skilled in the art, may be performed to allow the attachment of target receptors to the resonator.

Although some exemplary embodiments described above used an eroded optical fiber to evanescently couple light to the microresonator, other optical waveguides (such as, for example, tapered fiber, lithographed waveguide, rib waveguides, channel waveguides, nanowires, and other structures (or media) capable of supported a guided wavemode) may be used instead.

In at least some exemplary embodiments consistent with the present invention, the microresonator may have a diameter of between 300 μm or less, though resonators having other diameters may be used.

"Target receptor" is meant to describe any bionanoparticle or macromolecule (e.g., virus, protein, polynucleotide, polysaccharide, etc.) that can be attached to a micro resonator and receive a target entity of interest. Target receptors are intended to include numerous bionanoparticles and chemical classes, but will typically be organic molecules, or small organic compounds. Target receptors may include any functional groups (e.g., an amine, a carbonyl, a hydroxyl, a carboxyl group, sulfonyl, etc.) necessary for structural interaction (e.g., covalent bonding, hydrogen bonding, etc.) with target entities (e.g., proteins, antibodies, virus, etc.). Target receptors may include, for example, cyclical carbon or heterocyclic structures and/or aromatic or polyaromatic structures substituted with one or more of the above functional groups. Thus, target receptors may include biomolecules such as proteins, peptides, nucleic acids, saccharides, fatty acids, steroids, purines, pyrimidines, derivatives, and structural analogs or combinations thereof.

Target receptors can be obtained from a wide variety of sources including, for example, libraries of synthetic or natural compounds. Numerous means are available for random and directed synthesis of a wide variety of organic compounds and biomolecules, including expression of randomized oligonucleotides. Alternatively, libraries of natural compounds in the form of bacterial, fungal, plant and animal extracts are available to, or readily produced by, those skilled in the art. Additionally, natural or synthetically produced libraries and compounds may be modified through conventional chemical, physical and biochemical means. Known pharmacological agents may be subjected to directed or random chemical modifications, such as acylation, alkylation, esterification and/or amidification to produce structural analogs.

In some embodiments consistent with the present invention, the laser wavelength is 1060 nm, and has a drive power of between 7.3 and 42 µW, and preferably between 25 and 32 µW and for a $R \approx 50$ nm silica microsphere. Naturally, other laser wavelengths and drive powers may be used.

As used in this application (and as generally understood in the art), a "protein" includes at least two covalently attached amino acids, which includes proteins, polypeptides, oligopeptides and peptides. The protein may be made up of naturally occurring amino acids and peptide bonds, or synthetic peptidomimetic structures. Thus "amino acid", or "peptide residue", as used herein means both naturally occurring and synthetic amino acids. For example, homo-phenylalanine, citrulline and norleucine are considered amino acids in the context of this application.

The target receptors may be naturally occurring proteins, or fragments of naturally occurring proteins. Thus, for example, cellular extracts containing proteins, or random or directed digests of proteinaceous cellular extracts, may be used. In this way libraries of prokaryotic and eukaryotic proteins may be made for screening in the systems described herein. Particularly preferred in this embodiment are libraries of bacterial, fungal, viral, and mammalian (e.g., human) proteins.

In at least some embodiments consistent with the present invention, the target receptors are peptides. The peptides may be digests of naturally occurring proteins as is outlined above, random peptides, or "biased" random peptides. "Randomized" means that each nucleic acid and peptide consists essentially of random nucleotides and amino acids, respectively. These random peptides (or nucleic acids) may be chemically synthesized, and therefore may incorporate any nucleotide or amino acid at any position. The synthetic process can be designed to generate randomized proteins or nucleic acids, to allow the formation of all or most of the possible combinations over the length of the sequence, thus forming a library of randomized bioactive proteinaceous agents.

In at least some embodiments consistent with the present invention, the target receptors may be nucleic acids "Nucleic acid" or "oligonucleotide" means at least two nucleotides covalently linked together. A nucleic acid will generally contain phosphodiester bonds, although in some cases, as outlined below, nucleic acid analogs are included that may have alternate backbones, comprising, for example, phosphoramide, phosphorothioate, phosphorodithioate, O-methylphosphoroamidite, and peptide nucleic acid backbones and linkages. Other analog nucleic acids include those with positive backbones, non-ionic backbones and non-ribose backbones. Nucleic acids containing one or more carbocyclic sugars are also included within the definition of nucleic acids. The ribose-phosphate backbone may be modified to increase the stability and half-life of such molecules in physiological environments. In addition, mixtures of naturally occurring nucleic acids and analogs can be made. Alternatively, mixtures of different nucleic acid analogs, and mixtures of naturally occurring nucleic acids and analogs may be made. The nucleic acids may be single stranded or double stranded, as specified, or contain portions of both double stranded or single stranded sequence. The nucleic acid may be DNA, both genomic and cDNA, RNA or a hybrid, where the nucleic acid contains any combination of deoxyribo- and ribo-nucleotides, and any combination of bases, including uracil, adenine, thymine, cytosine, guanine, inosine, xanthanine, hypoxanthanine, isocytosine, isoguanine, and basepair analogs such as nitropyrrole and nitroindole, etc.

As described above generally for proteins, nucleic acids may be naturally occurring nucleic acids, random nucleic acids, or "biased" random nucleic acids. For example, digests of procaryotic or eukaryotic genomes may be used as is outlined above for proteins.

In general, the target receptors are designed to be complementary to a target entity, such that hybridization of the target entities and the target receptors occurs. It is not necessary for this complementarity to be perfect. For example, in the context of nucleic acid sequences, there may be one or more base pair mismatches that will interfere with hybridization between the target entity and the target receptor. However, if the number of mutations is so great that no hybridization can occur under even the least stringent of hybridization conditions, the target entity will not be considered to be complementary to the target receptor. "Substantially complementary" means that the target receptors are sufficiently complementary to the target entities to hybridize under selected reaction conditions.

In some embodiments consistent with the present invention, the target entity may be a "target sequence" which is a nucleic acid sequence on a single strand of nucleic acid. The target sequence may be a portion of a gene, a regulatory sequence, genomic DNA, cDNA, RNA including mRNA and rRNA, etc. The target sequence may be any length, with the understanding that longer sequences are more specific. As will be appreciated by those skilled in the art, the complementary target sequence may take many forms. For example, it may be contained within a larger nucleic acid sequence (e.g., all or part of a gene or mRNA, a restriction fragment of a plasmid or genomic DNA, among others.) Target receptors are made to hybridize to target sequences to determine the presence or absence of the target sequence in a sample.

In at least some embodiments consistent with the present invention, the target receptors may be organic chemical moieties.

In some embodiments consistent with the present invention, linkers may be used to attach the target receptors to the resonator, to facilitate good attachment, provide sufficient flexibility to allow good interaction with the target entities, and/or to avoid undesirable binding reactions.

In at least some embodiments consistent with the present invention, the bioactive target receptors are synthesized first, and then covalently attached to the resonator. As will be appreciated by those in the art, this will be done depending on the composition of the bioactive target receptors and the resonator. The functionalization of solid support surfaces such as certain polymers with chemically reactive groups such as thiols, amines, carboxyls, etc., is generally known in the art. Accordingly, "blank" resonators may be used that have surface chemistries that facilitate the attachment of the functionality desired. Some examples of these surface chemistries for blank microspheres include $NH_2$ (Amine), COOH (Carboxylic Acid), CHO (Aldehyde), $CH_2$—$NH_2$ (Aliphalic Amine), $CONH_2$ (Amide), $CH_2$—Cl (Chloromethyl), CONH—$NH_2$ (Hydrazide), OH (Hydroxyl), $SO_4$ (Sulfate), $SO_3$ (Sulfonate), and $ArNH_2$ (Aromatic Amine). These functional groups can be used to add any number of different bioactive agents to the resonator, generally using known chemistries. For example, bioactive target receptors containing carbohydrates may be attached to an amino-functionalized support; the aldehyde of the carbohydrate is made using standard techniques, and then the aldehyde is reacted with an amino group on the surface.

In an alternative embodiment, a sulfhydryl linker may be used. There are a number of sulfhydryl reactive linkers known in the art such as N-Succinimidyl-3-(2-PyridylDithio)-Propionate ("SPDP"), maleimides, .alpha.-haloacetyls, and pyridyl disulfides which can be used to attach cysteine containing proteinaceous agents to the resonator surface.

Alternatively, an amino group on the bioactive target receptor may be used for attachment to an amino group on the resonator surface. For example, a large number of stable bifunctional groups are well known in the art, including homobifunctional and heterobifunctional linkers.

In an additional embodiment, carboxyl groups (either from the surface of the resonator or from the target receptor) may be derivatized using well-known linkers. For example, carbodiimides activate carboxyl groups for attack by good nucleophiles such as amines. Proteinaceous target receptors may also be attached using other techniques known in the art, for example for the attachment of antibodies to polymers. It should be understood that the target receptors may be attached in a variety of ways, including those listed above. What is important is that manner of attachment does not significantly alter the ability of the target receptor to hybridize with the target entity.

CONCLUSIONS

Embodiments consistent with the present invention advantageously provide a resonator with a target receptor ribbon that is sensitive to the specific target entity to increase (e.g., maximize) resonance shifts, while preventing non-specific binding outside the ribbon of the resonator. Furthermore, embodiments consistent with the present invention make the surface of the resonator less susceptible to non-optimal binding as a result of changes in the physic-chemical properties of the (e.g., water) sample (e.g., conductivity, pH, etc.) being analyzed. Furthermore, the same laser for the surface modification (i.e., the fabrication) can also be used for detecting the target entity. In this way, the whispering gallery mode stimulated during the fabrication of the WGM sensor and during target entity sensing may be the same, leading to optimal overlap of the sensing mode and the surface modification.

What is claimed is:

1. A method for fabricating a sensor for determining the presence or concentration of a target entity in a medium, the method comprising:
   a) immersing a microresonator in a solution including target receptors;
   b) inducing light to resonate within the microresonator, thereby generating an attractive force between a ribbon surface area of the microresonator and the target receptors in the solution, the attractive force attracting the target receptors close enough to the ribbon surface area of the microresonator to permit chemical bonds to hold the target receptors to the ribbon surface area of the microresonator, wherein non-ribbon surface areas of the microresonator are substantially free of target receptors; and
   c) passivating the non-ribbon surface areas of the microresonator.

2. The method of claim 1 wherein the microresonator is optically coupled with an optical waveguide, and wherein the act of inducing light to resonate within the microresonator includes sourcing a laser light through the optical waveguide.

3. The method of claim 2 wherein the laser light is in the visible range having a wavelength between 400 nm and 750 nm.

4. The method of claim 2 wherein the laser light has a wavelength of between approximately 1.3 and 1.5 µm.

5. The method of claim 2 wherein the laser light has a wavelength in the near-infrared (NIR) range of between 750 nm and approximately 2.5 µm.

6. The method of claim 1 wherein the microresonator is attached to a core of an optical fiber, and wherein the act of inducing light to resonate within the microresonator includes sourcing a laser light through the optical fiber.

7. The method of claim 1 wherein the microresonator is has a geometry selected from a group of geometries consisting of (A) micro-sphere, (B) micro-ring, (C) micro-cylinder, (D) micro-racetrack, (E) micro-disk and (F) micro-toriod.

8. The method of claim 1 wherein the microresonator is a bottle microresonator.

9. The method of claim 1 wherein the optical waveguide is selected from a group consisting of (A) optical fiber, (B) rib waveguide, (C) channel waveguide and (D) nanowire.

10. The method of claim 1 wherein the solution is a low conductivity solution.

11. The method of claim 10 wherein the low conductivity solution is selected from a group consisting of (A) water and (B) heavy water.

12. The method of claim 10 wherein the low conductivity solution is a phosphate buffered saline solution.

13. The method of claim 1 wherein the chemical bonds are covalent bonds.

14. The method of claim 1 wherein the target receptors include antibodies.

15. The method of claim 1 wherein the target receptors include antibodies provided with a carboxyl group.

16. The method of claim 1 wherein the target receptors have a negative charge.

17. The method of claim 1 wherein the microresonator has a radius of 300 µm or less.

18. The method of claim 1 wherein the microresonator is made of a material selected from a group consisting of (A) glass, (B) silicon, (C) silicon nitride, (D) silicon oxynitride, (E) galiumn nitride, (F) gallium arsenide and (G) indium arsenide.

19. A method for fabricating a sensor for determining the presence or concentration of a target entity in a medium, the method comprising:
   a) immersing a microresonator in a solution including target receptors;
   b) inducing light to resonate within the microresonator, thereby generating an attractive force between a defined surface area of the microresonator and the target receptors in the solution, the attractive force attracting the target receptors to the defined surface area of the microresonator; and
   c) permitting chemical bonds to hold the target receptors to the defined surface area of the microresonator, wherein surface areas of the microresonator other than the defined surface area are substantially free of target receptors.

20. The method of claim 19 further comprising:
   d) passivating the surface areas of the microresonator other than the defined surface area

* * * * *